United States Patent
Berger et al.

(10) Patent No.: US 7,402,143 B2
(45) Date of Patent: Jul. 22, 2008

(54) BIO-FILTER PAD FOR FACILITATING THE DETECTION OF AN OCCURRENCE OF A PHYSIOLOGICAL ACTION AND METHOD THEREFOR AND FETAL ACTIVITY MONITORING APPARATUS

(75) Inventors: Avraham Berger, Givataim (IL); Ben Zion Haim, Kiryat Ono (IL); Baruch Meirovich, Hod Hasharon (IL); Avri Hazan, Givataim (IL)

(73) Assignee: Biopad Ltd, Givataim (IL)

( * ) Notice: Subject to any disclaimer, the term of this patent is extended or adjusted under 35 U.S.C. 154(b) by 251 days.

(21) Appl. No.: 10/522,545

(22) PCT Filed: Jul. 24, 2003

(86) PCT No.: PCT/IL03/00609
§ 371 (c)(1),
(2), (4) Date: Jan. 27, 2005

(87) PCT Pub. No.: WO2004/012598
PCT Pub. Date: Feb. 12, 2004

(65) Prior Publication Data
US 2006/0064040 A1    Mar. 23, 2006

(30) Foreign Application Priority Data
Aug. 1, 2002   (IL)   ...................... 151029

(51) Int. Cl.
*A61B 5/103* (2006.01)
*A61B 5/117* (2006.01)

(52) U.S. Cl. ...................... 600/595; 607/902
(58) Field of Classification Search ......... 600/586–588, 600/595; 73/654, 658; 607/902
See application file for complete search history.

(56) References Cited

U.S. PATENT DOCUMENTS

| | | | |
|---|---|---|---|
| 3,187,098 A * | 6/1965 | Farrar et al. | .................. 600/528 |
| 3,379,901 A | 4/1968 | Richards | |
| 3,488,821 A | 1/1970 | Richards | |
| 3,703,168 A | 11/1972 | Frink | |

(Continued)

FOREIGN PATENT DOCUMENTS

CN    1262918    8/2000

(Continued)

OTHER PUBLICATIONS

Fetal Movements in utero—A Review, I: The Physiology of Fetal Movements E. Sadovsky, M.D.; 1992; pp. 27-34.

(Continued)

*Primary Examiner*—Max Hindenburg
*Assistant Examiner*—Michael Apanius
(74) *Attorney, Agent, or Firm*—Harold L. Novick; Derek Richmond; The Nath Law Group

(57) ABSTRACT

The present invention facilitates the detection of an occurrence of a physiological action imparting a displacement to a body part at a natural frequency signature by virtue of a bio-filter pad including a viscoelastic interior for intimate juxtapositioning against the body part, and having a mechanical resonance frequency midway in the range of the frequency signature associated with the physiological action.

2 Claims, 5 Drawing Sheets

U.S. PATENT DOCUMENTS

| | | | |
|---|---|---|---|
| 3,763,851 A | | 10/1973 | Haff et al. |
| 3,934,577 A | | 1/1976 | Romani |
| 3,989,034 A | | 11/1976 | Hojaiban |
| 4,122,837 A | * | 10/1978 | Leonard ............... 600/587 |
| 4,143,650 A | | 3/1979 | Hatke |
| 4,781,200 A | | 11/1988 | Baker |
| 4,890,624 A | | 1/1990 | Ganguly et al. |
| 4,898,179 A | | 2/1990 | Sirota |
| 5,265,619 A | | 11/1993 | Comby et al. |
| 5,605,156 A | | 2/1997 | Drzewiecki et al. |
| 5,817,035 A | | 10/1998 | Sullivan |
| 6,024,711 A | | 2/2000 | Lentle et al. |
| 6,045,500 A | | 4/2000 | Bieniarz |
| 6,135,969 A | | 10/2000 | Hale et al. |
| 6,206,821 B1 | | 3/2001 | Kandori et al. |
| 6,275,719 B1 | | 8/2001 | Kandori et al. |
| 6,415,033 B1 | * | 7/2002 | Halleck et al. ............ 381/67 |
| 7,016,722 B2 | | 3/2006 | Prichep |
| 7,082,202 B1 | * | 7/2006 | Orten ..................... 381/67 |

FOREIGN PATENT DOCUMENTS

| | | |
|---|---|---|
| DE | 4225036 | 12/1993 |
| FR | 2602413 | 2/1988 |
| GB | 1348154 | 3/1974 |
| GB | 1369166 | 10/1974 |
| GB | 1398670 | 6/1975 |
| JP | 4309334 | 10/1992 |
| JP | 5000141 | 1/1993 |
| JP | 6296593 | 10/1994 |
| JP | 11089832 | 4/1999 |
| WO | WO86/02250 | 4/1986 |
| WO | WO89/04140 | 5/1989 |
| WO | WO99/52020 | 10/1999 |

OTHER PUBLICATIONS

IEEE Transactions on Biomedical Engineering vol. BME-27, No. 12, David Adler and Yona Mahler; Dec., 1980; pp. 738-740.

Classification of human fetal movement by Ilan Timor-Tritsch, M.D., Ivan Zador, M.Sc., Roger H. Hertz, M.D., Mortimer G. Rosen, M.D. American Journal of Obsterics and Gynecology, vol. 26, No. 1, pp. 70-77.

Recording of foetal movements: a comparison of three methods b y L. Valentin, K. Marsal and K. Lindstorm. Journal of Medical Engineering & Technology, vol. 10, No. 5 (Sep./Oct. 1986) pp. 239-247.

Human fetal respiratory movements: a technique for noninvasive monitoring with the use of a Tocodynamometer by Ilan E. Timor-Tritsch, Le-Roy J. Dierker, jr., Roger H. Hertz, Ivan Zador and Mortimer G. Rosen. Biol. Neonate 36: pp. 18-24 (1979).

A comparison between maternal, tocodynamometric, and real-time ultrasonographic assessments of fetal movement by Y. Sorokin, M.D., S. Pillay, Ph.D., L.J. Dierker, M.D., R. H. Hertz, M.D., M.G. Rosen, M.D. From the department of obstetrics and gynecology and the Permatal Clincal Research Center, Cleveland Metropolitan General Hospital/Case Western Reserve University, AM. J. Obstet. Gynecol. 140:456, 1981.

Ultrasonic evaluation of fetal body movements over twenty-four hour in the human fetus at twenty-four to twenty-eight weeks gestation by Constance Nesello-Paterson, Bsc, Renato Natale, MD, and Greg Connors, MD.

Differences in foetal heart rate variability from phonocardiography and abdominal electrocardiography by R. Ortiz, R. Gonzalez, M.A. Pena, S. Carrasco, M.J. Gaitan and C. Vegas. Journal of Medical Engineering & Technology, vol. 26, No.1, (Jan./Feb. 2002), pp. 39-45.

Correlation between electromagnetic recording and maternal assessment of fetal movement by E. Sadovsky, Y. Mahler, W.Z., The Lancet, May 26, 1973.

Maternal perception, tocodynamometric findings and real-time ultrasound assessment of total fetal activity by W.Schmidt, I. Cseh, K. Hara and F. Kubli. Department of Gynecology and Obstetrics, University of Heidelberg (F.R.G) Postgraduate Medical School, Department of Obstetrics and Gynecology, Szabolcs u. 35, H-1135 Budapest (Hungary) and Department of Obstetrics and Gynecology, University of Tokyo, Japan. International Journal of Gynecology & Obstetrics, vol.22, 1984, pp. 85-90.

Acoustics impedance of the maternal abdomen by George R. Wodicka, Journal of Acoustical Society of American, vol. 94, No. 1, Jul. 1993 pp. 13-18.

* cited by examiner

US 7,402,143 B2

BIO-FILTER PAD FOR FACILITATING THE DETECTION OF AN OCCURRENCE OF A PHYSIOLOGICAL ACTION AND METHOD THEREFOR AND FETAL ACTIVITY MONITORING APPARATUS

This application is the United States National Phase Filing of PCT Application PCT/I12003/000609 having an international filing date of Jul. 24, 2003.

FIELD OF THE INVENTION

The invention is in the field of medical diagnostic apparatus and methods for detecting an occurrence of a physiological action in general, and fetal activity in particular.

BACKGROUND OF THE INVENTION

Fetal activity has long been recognized as a good predictor of fetal well being as discussed in Fetal Movements In utero—A Review, Sadovsky, E., M.D., Isr. J. Obstet. Gynecol. 1992; 3:27-36. Fetal activity monitoring techniques run the gamut from an expectant mother's subjective assessment of fetal activity via fetal activity monitoring apparatus for monitoring her abdominal movements to in utero ultrasound based techniques for "looking inside" her uterus. Fetal activity monitoring apparatus is designed to monitor an expectant mother's abdominal movements within the range of 8-25 Hz which is the natural frequency signature of an expectant mother's abdomen. Such abdominal movements are assumed to be largely the result of fetal activity as opposed to uterine contractions, respiratory movements, maternal posture movements, and the like, and therefore the 8-25 Hz natural frequency signature of an expectant mother's abdomen is hereinafter coined as "natural fetal activity frequency signature".

An exemplary fetal activity monitoring apparatus is described in an article entitled "Measurement of Fetal Movements by Moving-Coil Transducer" by Adler D., et al., IEEE Transactions on Biomedical Engineering, Vol. BME-27, No. 12, December 1980 which employs two moving-coil transducers placed on the left and the right sides of an expectant mother's abdomen to pick up abdominal movements. This apparatus requires an about 80 dB electrical signal amplification for fetal activity detection at least partially being necessitated to overcome the transducers' attenuation of frequencies in the natural fetal activity frequency signature, and offset the apparatus' high sensitivity to electromagnetic interference (EMI).

SUMMARY OF THE INVENTION

Generally speaking, the present invention is directed toward a bio-filter pad capable of physically amplifying displacements within the range of a natural frequency signature associated with an occurrence of a physiological action for facilitating detection of such an occurrence. This is achieved by the bio-filter pad having a mechanical resonance frequency preferably midway in the range of the natural frequency signature, and a transducer for intimate mechanical coupling therewith also preferably tuned to the same mechanical resonance frequency to increase physical amplification of a displacement, thereby lessening electrical signal amplification requirements by a suitable physiological activity recorder. Transducers employed for implementing the present invention are preferably of the type whose resonant frequency are readily tunable to the desired frequency range, for example, moving coil transducers, however, other types of transducers may also be employed.

At the present time, it is envisaged that the primary application of the present invention will be for fetal activity monitoring purposes in general, and home based fetal activity monitoring purposes in particular but it is also envisaged that the bio-filter pad of the present invention can be adapted for use in sport medicine, rehabilitation, and the like. For fetal monitoring purposes, a bio-filter pad and a transducer preferably each have the same mechanical resonance frequency midway in the range of the natural fetal activity frequency signature whereby they are capable of yielding from about 20 to about 50 physical amplification of an abdominal displacement. By virtue of this physical amplification, a suitably tuned transducer and a fetal activity recorder together constituting fetal activity monitoring apparatus need only a combined about 45 dB electrical signal amplification as opposed to the hitherto required 80 dB electrical signal amplification in the above-mentioned Adler article, thereby also inherently beneficially reducing the latter's EMI sensitivity.

BRIEF DESCRIPTION OF THE DRAWINGS

In order to understand the invention and to see how it can be carried out in practice, preferred embodiments will now be described, by way of a non-limiting example only, with reference to the accompanying drawings in which similar parts are likewise numbered, and in which.

DETAILED DESCRIPTION OF PREFERRED EMBODIMENTS

Figure 1:
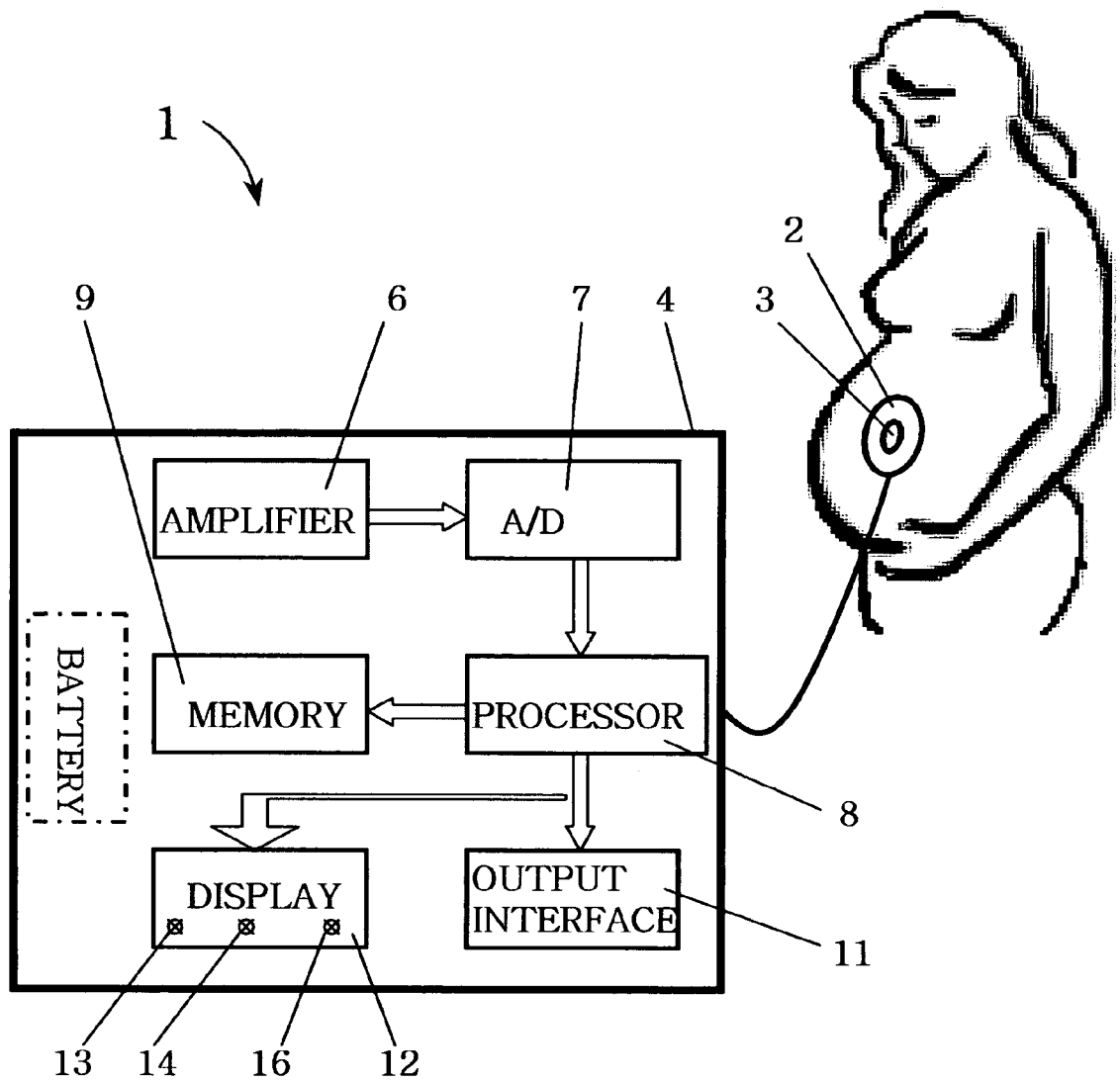
FIG. 1 is a schematic representation of a first preferred embodiment of a fetal activity monitoring system in accordance with the present invention including a bio-filter pad, a transducer and a fetal activity recorder.
Figure 2:
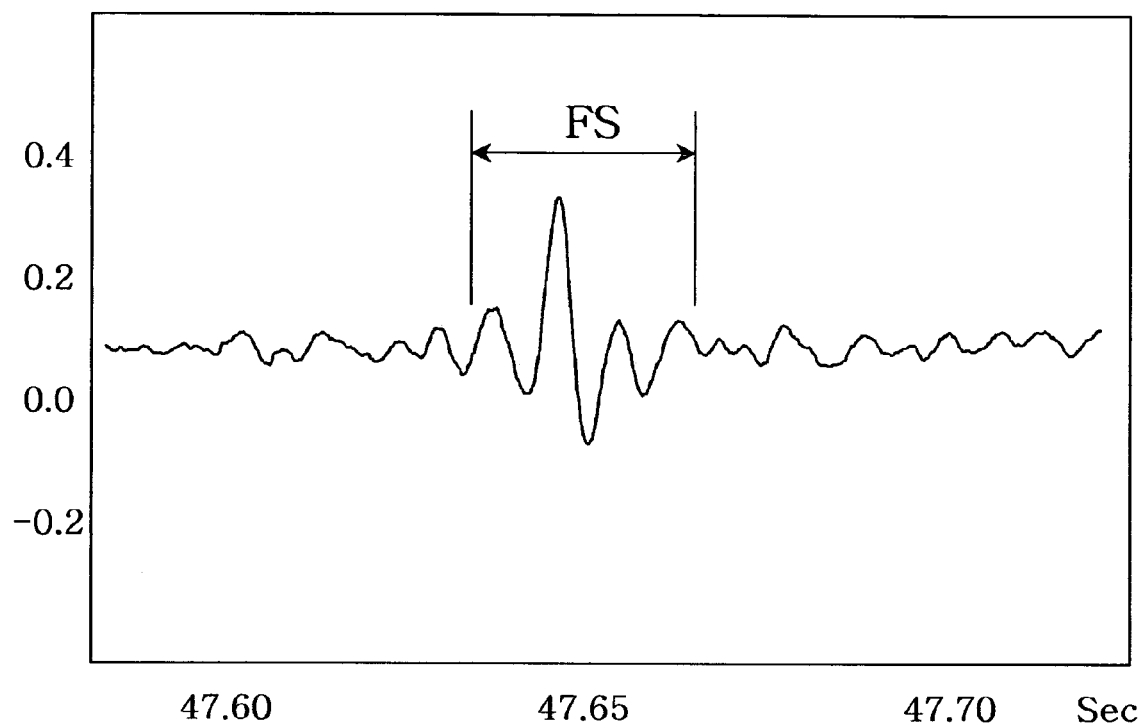
FIG. 2 is a graph showing the natural fetal activity frequency signature of an expectant mother's abdomen.

FIG. 1 shows a fetal activity monitoring system 1 suitable for home use for providing a visual indication regarding the prevailing level of fetal activity based on detecting an expectant mother's abdominal movements having a typical natural fetal activity frequency signature FS (see FIG. 2). The fetal activity monitoring system 1 includes a bio-filter pad 2 adapted for removable intimate adhesion to her abdomen, and having a moving coil transducer 3 centrally disposed thereon for picking up her abdominal movements. The transducer 3 is connected to a credit-card like, battery powered, fetal activity recorder 4 having an amplifier 6, an A/D converter 7, a signal processor 8, a memory 9, an output interface 11, for example, RS-232, and a fetal activity display 12 for comparing the prevailing fetal activity during a fetal activity monitoring session to a regular level of fetal activity determined on the basis of historical information. The fetal activity display 12 has three LEDs: a green LED 13 for indicating a regular level of fetal activity, an orange LED 14 for indicating a marginally lower than regular level of fetal activity, and a red LED 16 for indicating a significantly lower than regular level of fetal activity. The transducer 3 and the fetal activity recorder 4 have a combined electrical signal amplification in the order of about 45±5 dB.

Figure 3:
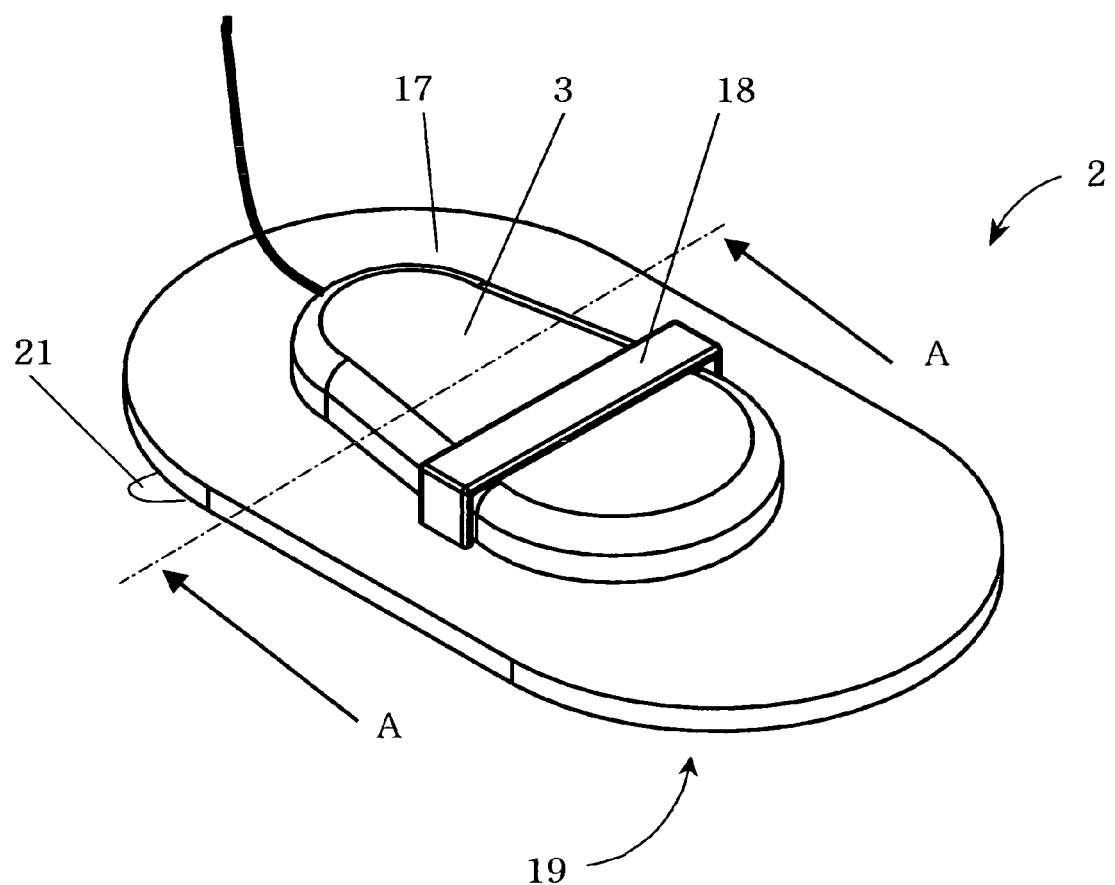
FIG. 3 is a pictorial representation of the bio-filter pad of FIG. 1.
Figure 4:
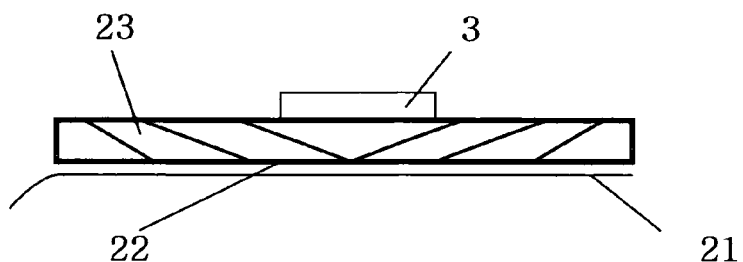
FIG. 4 is a cross section view of the bio-filter pad of FIG. 1 along line A-A in FIG. 3.
Figure 5:
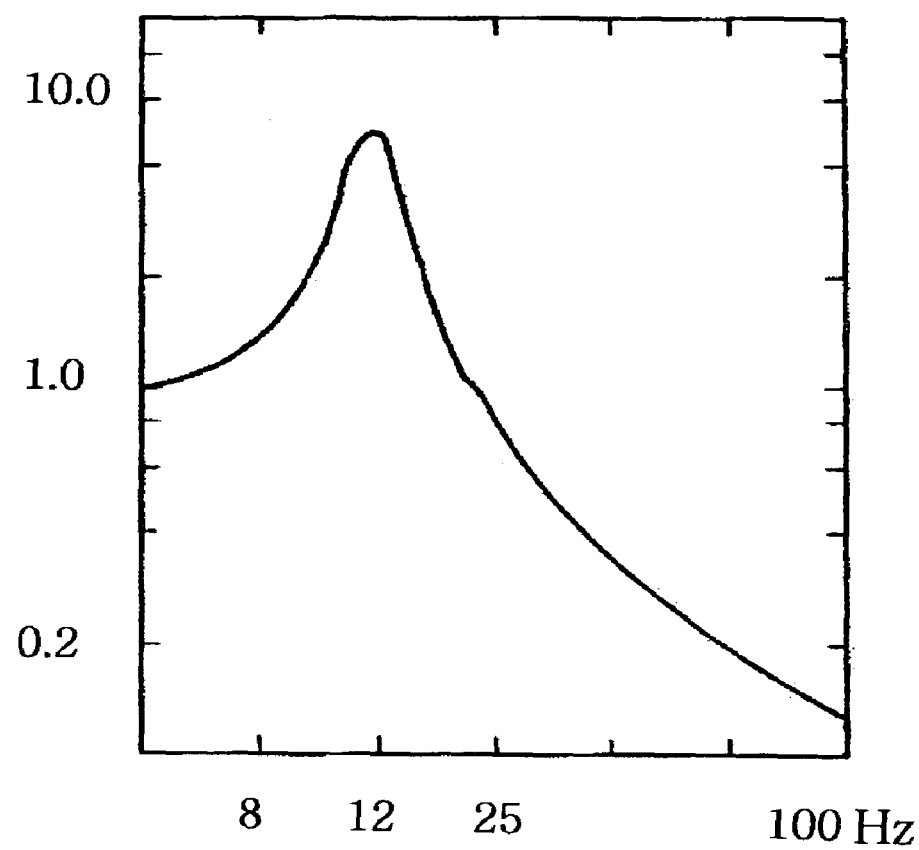
FIG. 5 is a graph showing the transmissibility response curve of the bio-filter pad of FIG. 1.

FIG. 3 shows that the bio-filter pad 2 has a topside 17 formed with a resiliently elastic restraining member 18 for intimately mechanically coupling the transducer 3 to the bio-filter pad 2 on its being slided thereunder, and an underside 19 with a peal-off protective liner 21 for exposing an adhesive surface 22 enabling the removable intimate adhesion of the bio-filter pad 2 to an expectant mother's abdomen. The bio-filter pad 2 is preferably circular with a diameter within the range of about 10 cm to about 25 cm, and has a thickness within the range of about 1 mm to about 5 mm. The bio-filter pad 2 has a viscoelastic interior 23 with concentric sections for focusing mechanical energy imparted thereto arising from abdominal movements towards the transducer 3 for enabling detection of most if not all fetal activity and not just limb movements directed towards the transducer 3 (see FIG. 4) The viscoelastic interior 23 may be constituted by a solid material, a gel like material, a fluid material, or a combination thereof. The bio-filter pad 2 has a 12 Hz mechanical resonance frequency for physically amplifying displacements within the natural frequency fetal activity signature (see FIG. 5), as does the transducer 3. The mechanical resonance frequencies of the bio-filter pad 2 and the transducer 3 can be tested by knocking on them. The mechanical coupling between the bio-filter pad 2 and the transducer 3 are such that they yield from about 20 to about 50 physical amplification of an abdominal displacement, thereby accentuating a natural fetal activity frequency signature.

The fetal activity monitoring system typically replaces an expectant mother's subjective assessment of fetal activity in an otherwise conventional fetal activity monitoring program. Thus, in accordance with her fetal activity monitoring program, she removes a peal-off protective liner from a bio-filter pad, intimately adheres the bio-filter pad onto her abdomen, couples the transducer to the bio-filter pad, and proceeds to record her abdominal movements. In the normal course of events, the green LED will be illuminated and no special action need to be taken. In the event that either the yellow LED or red LED is illuminated during a fetal activity monitoring session, she takes the fetal activity recorder storing all historical fetal activity information to a medical specialist for a professional diagnosis.

Figure 6:
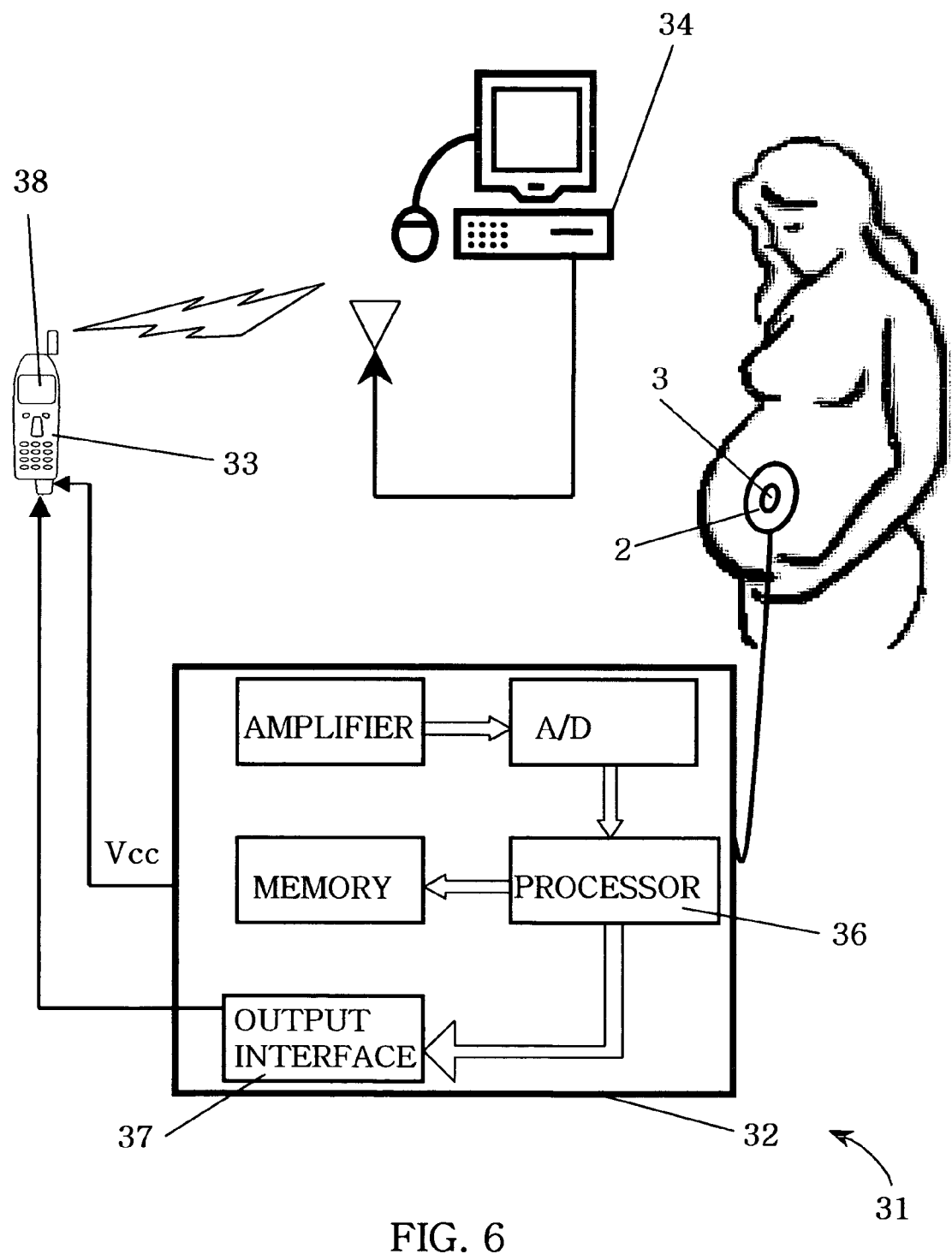
FIG. 6 is a schematic representation of a second preferred embodiment of a fetal activity monitoring system in accordance with the present invention.

FIG. 6 shows a fetal activity monitoring system 31 similar to the fetal activity monitoring system 1 except that instead of its fetal activity recorder 32 being a standalone unit, it is intended for removable attachment to a mobile telephone 33 for both being powered thereby, and for connection to a remote server 34 for data processing purposes. To this end, the fetal activity recorder 32 includes a data compression processor 36 for compressing a fetal activity recording for selective transmission to the remote server 34, and an audio output 37 for connection to the mobile telephone's audio input. The results of a fetal activity monitoring session are preferably transmitted by SMS for display on the mobile telephone's display 38.

While the invention has been described with respect to a limited number of embodiments, it will be appreciated that many variations, modifications, and other applications of the invention can be made within the scope of the appended claims. For example, a bio-filter pad may be oval shaped, and may employ different restraining techniques for juxtaposing a transducer against its topside. Also, a recorder, for example, the fetal activity recorders 4 and 36, may be integrally formed with a transducer.

The invention claimed is:

1. A disposable single use bio-filter pad for use in the detection of fetal activity occurrences imparting abdominal displacements to an expectant mother's abdomen at a natural fetal activity frequency signature within the range of 8-25 Hz, the bio-filter pad being intended for use with a discrete transducer sensitive to an expectant mother's abdominal displacements, the bio-filter pad being sized and shaped for conforming to an expectant mother's abdomen and comprising:
   (a) viscoelastic interior with a topside and an underside substantially opposite and parallel to said topside for respectively facing away from and toward an expectant mother's abdomen, and having a mechanical resonance frequency midway in the range of the 8-25 Hz natural fetal activity frequency signature for amplifying an expectant mother's abdominal displacements on being intimately juxtaposed against her abdomen;
   (b) peel-off protective liner for exposing an adhesive surface suitable for removable intimate adhesion of at least a portion of said underside onto the expectant mother's abdomen; and
   (c) a restraining member on said topside for slidingly receiving the transducer in a direction substantially co-directional with said topside and underside for removably intimately mechanically coupling the transducer to a central location on said topside.

2. The pad according to claim 1 wherein said viscoelastic interior has concentric sections for focusing mechanical energy imparted to the bio-filter pad due to the expectant mother's abdominal displacements towards the centrally located transducer.

* * * * *